United States Patent [19]

Pohl et al.

[11] Patent Number: 5,571,725
[45] Date of Patent: Nov. 5, 1996

[54] METHOD FOR PRECIPITATION OF INSOLUBLE SALTS IN DIVALENT ION-FORM MATERIALS

[75] Inventors: Christopher A. Pohl, Union City, Calif.; Archava Siriraks, Bangkok, THX; Rosanne W. Slingsby, Pleasanton; Harpreet S. Dhillon, Santa Clara, both of Calif.

[73] Assignee: Dionex Corporation, Sunnyvale, Calif.

[21] Appl. No.: 398,117

[22] Filed: Mar. 3, 1995

[51] Int. Cl.$^6$ .......................... G01N 30/02; G01N 30/96
[52] U.S. Cl. .......................... 436/161; 436/79; 436/110; 436/124; 436/125; 436/175; 436/177; 436/178; 73/61.55; 210/656; 210/660
[58] Field of Search .......................... 436/79, 110, 124, 436/125, 161, 175, 177, 178; 210/656, 198.2, 660; 73/61.55

[56] References Cited

U.S. PATENT DOCUMENTS

| | | | |
|---|---|---|---|
| 3,926,559 | 12/1975 | Stevens | 436/161 |
| 4,357,143 | 11/1982 | Scott | 436/161 |
| 4,814,281 | 3/1989 | Byers | 436/150 |
| 5,227,053 | 7/1993 | Brym | 210/143 |

OTHER PUBLICATIONS

Alltech Bulletin #264.
Joyce et al. (1994) J. Chromatog. 165–171.
Alltech Data Sheet #D70264.

*Primary Examiner*—Jeffrey Snay
*Assistant Examiner*—Jan M. Ludlow
*Attorney, Agent, or Firm*—Flehr, Hohbach, Test, Albritton & Herbert

[57] ABSTRACT

Selected polyvalent anions or cations are removed from a liquid sample stream as a pretreatment for the analysis of the liquid sample stream. A stream containing anions of interest, precipitable anions (e.g. sulfate ions) to be removed and an added displacing salt flow through a first cation exchange resin bed having precipitable exchangeable polyvalent ions (e.g. barium ions). Displacing polyvalent cation (e.g. calcium) displaces the exchangeable polyvalent ion from the cation exchange resin into the liquid sample at sufficient concentration to cause the precipitable anion and exchangeable cation to form a precipitate which remains in the resin bed and is thus is removed from the sample stream. Then the anions of interest in the soluble portion of the liquid sample stream are separated and detected. The invention is also applicable to the removal of precipitable cations (e.g. barium ions) by reversing the roles of the anions and cations.

21 Claims, No Drawings

METHOD FOR PRECIPITATION OF INSOLUBLE SALTS IN DIVALENT ION-FORM MATERIALS

BACKGROUND OF THE INVENTION

In certain instances, anions (e.g. sulfate ions) are removed from liquid samples by passing through a packed bed of cation exchange resin with an exchangeable polyvalent cation (e.g. in barium-form) with which the sulfate ion forms a precipitate. Such removal is performed in a pretreatment step prior to the separation and detection of other anions in a sample to prevent adverse effects on performance. The barium ion is displaced from the ion exchange resin by other cations in the sample so that precipitation can occur. However, since barium is a divalent cation, the cation exchange resin has much higher selectivity for barium than the monovalent ions, such as sodium, present in abundance in a typical sample. Polyvalent cations are not normally present in a sample at a high enough concentration to displace sufficient barium for complete sulfate removal. Therefore, the effectiveness of removal of sulfate from liquid samples by precipitation in barium-form media depends on the composition of the sample matrix. This leads to unpredictable results for samples of unknown cation composition. This same problem applies to the removal of cations (e.g. barium ions) using a polyvalent anion exchange bed.

It is an object of the invention to improve the removal of selected anions from a liquid sample, using a packed bed.

SUMMARY OF THE INVENTION

In accordance with the present invention, selected polyvalent anions or cations are removed from a liquid sample stream as a pretreatment for the analysis of the liquid sample stream. First, anion removal will be discussed. The stream containing anions of interest, precipitable anions (e.g. sulfate ions) to be removed and an added displacing salt flow through a first cation exchange material (e.g. a resin bed) having precipitable exchangeable polyvalent ions (e.g. barium ions). The displacing salt is formed of a displacing polyvalent cation (e.g. calcium) and a counterion to the displacing ion. The displacing cation displaces the exchangeable polyvalent ion from the cation exchange material into the liquid sample at sufficient concentration to cause the precipitable anion and exchangeable cation to form a precipitate which remains in the resin bed and is thus is removed from the sample stream. Then the anions of interest in the soluble portion of the liquid sample stream are separated and detected.

The counterion (e.g. chloride) to the displacing cation may be removed from the sample stream by passing the liquid sample through second cation exchange resin having an exchangeable cation (e.g. silver) capable of precipitating with the counterion. Also, a salt having an anion of the formula $XO_3^{y-}$ may added to improve the recovery of selected anions of interest (e.g. bromate ion).

The invention is also applicable to the removal of precipitable cations (e.g. barium ions) by reversing the roles of the anions and cations.

DETAILED DESCRIPTION OF THE PREFERRED EMBODIMENTS

The present system is applicable to the removal of a precipitable anion or cation in a liquid sample prior to analysis of other sample ions of interest.

Typical anions of interest in a liquid sample include bromate, nitrite and nitrate. Typical cations of interest in a liquid sample include calcium, magnesium, potassium, sodium and strontium.

In its broadest form, the invention includes a pretreatment step prior to separation of anions or cations of interest in a liquid sample. It is applicable to pretreatment in which a precipitable anion is removed by precipitation with the precipitable exchangeable polyvalent ions of opposite charge of an ion exchange resin material. This invention is specifically directed to the improvements to such a pretreatment system.

The terms "exchangeable cation or anion" refers to a precipitable polyvalent ion with a valency of at least two, and included a valency of three or more, capable of performing the above function. Exchangeable cations include barium, aluminum, calcium, and iron. Exchangeable anions include sulfate, phosphate, and chromate.

The terms "cation or anion exchange resin material" includes conventional ion exchange resin beds or other materials having exchangeable ions capable of being removed and forming a precipitate with the precipitable anion or cation.

The present invention broadly relates to the improvement of the removal of the precipitable anion or cation by the addition of a displacing salt. Referring to anion analysis, the displacing salt includes a displacing polyvalent cation and a counterion to the displacing cation. The displacing salt facilitates displacement of the exchangeable cation from the cation exchange material into the liquid sample under conditions to cause the precipitable anion and exchangeable cation to precipitate.

The displacing polyvalent cation is of a type that any soluble portion left after precipitation does not interfere with the subsequent separation and detection of the separated anions of interest. Effective displacing cations include divalent or higher valency cations including magnesium, calcium, divalent or higher quaternary ammonium compounds, and the like. To remove sulfate on a barium-form ion exchange material cartridge, calcium or magnesium are effective displacing cations.

The improvement in efficiency is due to the displacing polyvalent cation providing a driving force for facilitating the displacement of the exchangeable polyvalent cation for precipitation with the precipitable anion to be removed. To accomplish this, a suitable ratio range of displacing cation to exchangeable cation is 1:1 to 20:1, preferably about 1.5:1 to 3:1 for calcium and magnesium displacing ions.

Suitable conditions for the above precipitation reaction in the presence of the displacing salt are as follows. In the anion case, the most typical precipitable anion is sulfate, which can be present at concentrations ranging from 1 to 100,000 mg/L (1M) in a sample. A typical concentration of sulfate is about 400 mg/L. When calcium is used as the displacing ion, it is spiked into the sample at 0.005M, which is about a ratio of 2:1 to barium in the resin bed. This process is most efficient at flow rates less than 2 mL/min. As the barium is displaced from the resin and enters the liquid phase surrounding the ion exchange resin, it is available to precipitate with the sulfate in the sample. Although barium sulfate will precipitate when the solubility product exceeds $1.1 \times 10^{-10}$ (Reference: Lange's Handbook of Chemistry, John A. Dean, 14th Ed., 1992, p. 8.6) this solubility is finite and some barium sulfate can be resolubilized in the device. Therefore, somewhat higher concentrations of barium are very desirable. A typical resin bed will contain ion exchanger with an ion exchange capacity of 5 mEq/g on a dry basis and contain about 35% water. The ion exchange capacity can vary from 2–10 mEq/g and the water content can vary from 20–70%. In the form of a porous sheet, the ion exchange capacity in the range of 2–10 mEq/g with a water content of 20–70%.

In the cation case, a typical cation of interest is barium in the range of 1–100,000 mg/L. A typical concentration is about 50 mg/L. Sulfate-form anion exchange material is used. When tartrate is used as the displacing ion, it is spiked into the sample at 0.005M. The ratio of displacing ion to exchangeable ion, in this example is about 14:1. Barium sulfate will precipitate when the solubility product exceeds $1.1 \times 10^{-10}$ (Reference: Lange's Handbook of Chemistry, John A. Dean, 14th Ed., 1992, p. 8.6). A typical resin bed will contain ion exchanger with an ion exchange capacity of 3 mEq/g on a dry basis and contain about 35% water. The ion exchange capacity can vary from 20–70%. In the form of a porous sheet, the ion exchange capacity is the range of 2–10 mEq/g with a water content of 20–70%.

The counterion to the displacing cation also is of a form which does not interfere with the separation and detection of the anions of interest. For the removal of sulfate from the liquid, suitable counterions to the displacing cation include chloride, bromide, iodide, cyanide, or thiocyanate.

If the counterion to the displacing cation would interfere with separation or detection, it should be removed prior to separation. In a preferred form of removal, the counterion is precipitated in a manner similar to that of the removable precipitating anion. For example, it can be removed by passing the liquid sample stream through a second cation exchange resin material having an exchangeable cation capable of precipitation with it. In the case of chloride concentration, a suitable cation exchange resin material is in the silver form. Here, a typical liquid sample includes sufficient monovalent cations (e.g. sodium) to displace the silver ion into solution to precipitate with the chloride ion.

Use of silver-form resin to remove chloride ion prior to ion chromatography is described in Joyce, Robert J. and Harpreet S. Dhillon, *Trace Level Determination of Bromate in Ozonated Drinking Water Using Ion Chromatography*, J. Chromatogr. A, 671 (1994) 165–171.

The invention is also applicable to the use of a trivalent exchangeable cation such as aluminum for the removal of a polyvalent precipitable anion such as phosphate. In this instance, a suitable displacing polyvalent cation, preferably, trivalent, is added to displace the exchangeable cation. Such suitably polyvalent cations include bis(trimethylammonio)dimethylammonium trichloride, and octamethyldiethylenetriammonium trihalide.

The present invention is particularly useful for the determination of low levels of bromate (e.g. less than one ppm). If such low concentrations of bromate are to be determined, large sample volumes must be used to achieve good sensitivity. Large concentrations (e.g. higher than 30 mg/L) of anions such as sulfate adversely effect bromate analysis by causing lack of reproducibility in retention time and pre-concentration efficiency in the chromatography.

It is difficult to effectively recover and analyze for bromate ion using a barium-form ion exchange material to remove sulfate as a barium sulfate precipitate because the bromate may "ion exchange or coprecipitate" with the barium into the matrix of the barium sulfate. It has been found that anions of the formula $XO_3^{y-}$ may be added to improve the efficiency of analyzing for bromate. As defined herein, X may be C, I, N, or Cl.

Suitable concentrations of $XO_3^{y-}$ (e.g., carbonate) to improve bromate recovery are on the order of 10 mg/L to 200 mg/L. Preferably, the carbonate is present in sufficient quantity to provide a final concentration of about 100 ppm, the higher limit being determined by solubility.

Normally, calcium carbonate cannot be used as the displacing salt because it is relatively insoluble. Magnesium should not be added to the sample at a final concentration in excess of 0.005M, which is the solubility limit of magnesium carbonate. In order to avoid diluting the sample too much, it is most practical to prepare a 100× concentrate of the spiking solution and spike at 1:100 in the sample. Therefore, it is advantageous to add magnesium chloride and sodium carbonate separately, rather than magnesium carbonate. Depending on the sample, magnesium can be added at a concentration as high as 0.020M, preferably in the range of 0.001–0.010M. The chloride may be removed by a conventional silver-form ion exchange material.

Where carbonate ion is added, it may be desirable to remove it prior to separation. One method of removal would be to pass the solution after precipitation of the precipitable anion through an ion exchange material in hydronium ion-form. In this instance, the carbonate ion is acidified to carbon dioxide according to the following formula:

$$CO_3^{2-} + 2H^+ \rightleftharpoons CO_2\uparrow + H_2O.$$

The carbon dioxide gas may be sparged (e.g. with an inert gas for five minutes).

It is most useful to add carbonate at a concentration in the sample of 100 mg/L. The useful range is about 10–200 mg/L, the upper limit set by solubility in the sample matrix.

The present invention may also be employed for the removal of a precipitable cation. For example, a precipitable cation (e.g. barium ion) may be removed by an anion exchange resin material having an exchangeable polyvalent anion (e.g. sulfate ion) which forms a precipitate with the cation. Another suitable precipitable cation is aluminum. Another suitable exchangeable polyvalent anion is phosphate.

For cation analysis, the displacing salt includes a displacing polyvalent anion and a counterion to the displacing cation. Suitable displacing polyvalent anions include tartrate, oxalate, and chromate. Tartrate is particularly effective displacing anion for the barium sulfate system. The above conditions of use are also applicable.

The counterion to the displacing anion is one that either does not interfere with the separation or which can be readily removed from the system. For example, a suitable counterion for a tartrate ion is silver which can be removed from the system prior to analysis by passing through a second anion exchange resin material having an exchangeable anion (e.g. chloride) capable of precipitation with the counterion. Other exchangeable anions include bromide, iodide, and thiocyanate.

The present invention may use any of a number of conventional pretreatment ion exchange materials in resin bed or sheet form. For example, the following materials are available.

(1) barium-form ion exchange resin bed and/or porous sheet cartridge. Novo-Clean IC-Ba porous sheet described in Alltech Bulletin #264, Dionex OnGuard-Ba resin bed described in Dionex publication p/n 032943, Alltech Max-Clean IC-BA resin bed.

(2) silver-form ion exchange resin bed and/or porous sheet cartridge. Dionex OnGuard-Ag resin bed noted in J. Chromatogr. A 671(1994) 165–171 (noted above) and in Dionex publication p/n 032943, Novo-Clean IC-Ag porous sheet described in Alltech Bulletin #264, Alltech Maxi-Clean IC-Ag resin bed.

(3) hydronium ion-form ion exchange resin bed and/or porous sheet cartridge. There are a number of commercially available hydronium ion-form resin or membrane devices. (Dionex OnGuard-H resin bed described in Dionex publication p/n 032943, Novo-Clean IC-H porous sheet described in Alltech bulletin #254, Alltech Maxi-Clean IC-H packed resin bed, Waters MilliTrap H* Membrane cartridges, Bio-Rad Poly-Prep Column p/n 731-6213 and 731-6214, Varian Bond Elut SCX, Varian Bond Elut CBA, Varian Bond Elut PRS.) Such devices may be converted to silver or barium form (e.g., as described in Alltech Data Sheet D70264.)

(4) other commercial columns ion exchange resin bed and/or porous sheet cartridge. (Dionex OnGuard-A, bicarbonate-form anion exchange resin bed, Alltech Maxi-Clean IC-OH hydroxide-form anion exchange bed, 3M EMPORE porous sheets, Bio-Rad Poly-Prep columns with Cl-form and formate-form anion exchange resin, Varian Bond Elut SAX.

In the above system pretreatment may be used prior to separation of the anions of interest in any conventional technique. Before separation, it may be desirable to preconcentrate the sample (e.g. by the technique described in U.S. Pat. No. 4,314,823, and Joyce, Robert J. and Harpreet S. Dhillon, *Trace Level Determination of Bromate in Ozonated Drinking Water Using Ion Chromatography*, J. Chromatog. A, 671 (1994) 165–171, incorporated herein by reference). Suitable forms of separation include capillary electrophoresis, liquid chromatography, and, particularly, ion chromatography. Any conventional detector (e.g. conductivity detection for ion chromatography) may be employed.

The following examples illustrate the present invention.

EXAMPLE 1

Sample: Trace Anions (Chloride, Nitrate, Nitrite, and Phosphate) in 0.4M Sodium Sulfate 1. Prepare sample by spiking in calcium as calcium chloride to a final concentration of 0.005M.

2. Prepare sample preparation cartridge by packing with barium-form cation exchange resin. Barium-form cation exchange resin is characterized by being a fully sulfonated styrene-divinylbenzene resin, 1 g/cartridge, 5 mEq/cartridge on a dry basis.

3. Attach the barium-form cartridge to a silver-form cartridge of the type set forth above.

4. Pass sample through the barium-form cartridge followed by a silver-form cartridge. (The silver-form cartridge removes halides such as chloride by precipitation of AgCl.) Observe improved sulfate removal as compared to passing the same sample through the cartridge without the addition of calcium. The chloride is removed by the silver-form cartridge.

Features and Benefits

The following table shows the improved removal of sulfate from a sodium sulfate sample when the sample is spiked to 0.005M in calcium.

| Sample Sulfate (mg/L) from $Na_2SO_4$ | Residual Sulfate (mg/L) (sample w/o $Ca^{2+}$ added) | Residual Sulfate (mg/L) (sample with $Ca^{2+}$) |
|---|---|---|
| 400 | 70 | 4 |

Note that 70 ppm sulfate is left in the same sample originally containing 400 ppm sulfate when no calcium is added to the sample. When the sample is spiked to a final concentration of 0.005M calcium with calcium chloride, only 4 ppm sulfate remains.

EXAMPLE 2

Sample: Trace Cations in 100 mg/L Barium Chloride Solution

Cartridge contains fully aminated styrene-divinylbenzene anion exchange resin in the sulfate form. The sample is spiked to contain 0.005M tartrate and improved removal of barium from the sample is observed,

| Sample | Residual $Ba^{2+}$ w/o tartrate | Residual $Ba^{2+}$ w/tartrate |
|---|---|---|
| 100 mg/L $Ba^{2+}$ | 44 | 1.7 |

EXAMPLE 3

Removal of sulfate with barium cartridge for bromate analysis, adding magnesium and carbonate as magnesium chloride and sodium carbonate.

Sample: Bromate in Ozonated Drinking Water, <1 mg/L.

The drinking water may contain more than 100 mg/L chloride and more than 200 mg/L sulfate.

The cartridge train is shown in FIG. 1.

1. Spike sample to 0.005M Magnesium with 0.5M magnesium chloride hexahydrate.
2. Spike sample to 100 mg/L carbonate with 10,000 mg/L sodium carbonate.
3. Pass sample through the cartridge train at up to 2 mL/min, discarding the first 3 mLs.
4. Inject 3.5 mLs sample into a trace level bromate ion chromatography system as described in Joyce, Robert J. and Harpreel S. Dhillon, *Trace Level Determination of Bromate in Ozonated Drinking Water Using Chromatography*, J. Chromatogr. A, 671 (1994) 165–171.

| | Table of Bromate Recovery | |
|---|---|---|
| Matrix | 1 ug/L $BrO_3$ recovery w/o spiking | 1 ug/L $BrO_3$ recovery w/spiking |
| 100 mg/L $SO_4^{2-}$ | 50% | 95% |

EXAMPLE 4

Sample: Trace Ions in 400 mg/L Phosphate

Cartridge contains fully sulfonated styrene-divinylbenzene cation exchange resin in the aluminum form. The sample is spiked with a trivalent cation (0.005M bis(trimethylammonio)-dimethylammonium trichloride (BTMA) and improved removal of phosphate from the sample is observed.

| Table of Phosphate Recovery | | |
| --- | --- | --- |
| Sample | Residual $PO_4^{3-}$ w/o $PO_4^{3-}$ | Residual $PO_4^{3-}$ w/BTMA |
| 100 mg/L $PO_4^{3-}$ | 100 mg/L | 5 mg/L |

What is claimed is:

1. In a pretreatment and separation method for the removal or a precipitable anion in a liquid sample and subsequent detection of other anions of interest in said liquid sample, the steps of
   (a) flowing a stream of the liquid sample, containing said anions of interest, precipitable anion, and an added displacing salt through a first cation exchange resin material having a precipitable exchangeable polyvalent cation, said displacing salt comprising a displacing polyvalent cation and a counterion to said displacing cation, to displace said precipitable exchangeable polyvalent cation ion from said cation exchange material into said liquid sample under conditions to cause said precipitable anion and exchangeable polyvalent cation to form a precipitate,
   (b) separating from each other the anions of interest in the soluble portion of said liquid sample stream, and
   (c) detecting the separated anions of interest.

2. The method of claim 1 in which said exchangeable cation is selected from the group consisting of barium, aluminum, calcium, and iron.

3. The method of claim 1 in which said precipitable anion is phosphate and said exchangeable cation is aluminum.

4. The method of claim 1 further comprising, prior to step (c), the step of
   (d) removing said counterion to said displacing cation from said liquid sample stream.

5. The method of claim 4 in which step (d) is performed by passing said liquid sample stream through a second cation exchange resin material having an exchangeable cation capable of precipitation with said counterion to said displacing cation.

6. The method of claim 1 further comprising adding a salt having an anion of the formula $XO_3^{y-}$, in which X is selected from the group consisting of C, I, N, and Cl, to improve the recovery of at least one anion of interest.

7. The method of claim 6 in which at least one anion of interest is bromate ion.

8. The method of claim 7 further comprising, prior to step (b), removing said $XO_3^{y-}$ anion from said liquid sample stream.

9. The method of claim 8 in which said $XO_3^{y-}$ anion is $CO_3^{-2}$ and is removed by acidifying said liquid sample stream to form a gas and venting said gas from said liquid stream.

10. The method of claim 6 in which said $XO_3^{y-}$ salt is magnesium carbonate.

11. The method of claim 1 in which said precipitable anion is sulfate and said exchangeable cation is barium.

12. The method of claim 11 in which said displacing cation is calcium or magnesium.

13. The method of claim 11 in which said counterion to said displacing cation is chloride, bromide, iodide, cyanide, or thiocyanate.

14. The method of claim 11 in which said counterion to said displacing cation is chloride.

15. In a pretreatment and separation method for the removal of a precipitable cation in a liquid sample and subsequent detection of other cations of interest in said liquid sample, the steps of
   (a) flowing a stream of the liquid sample, containing said cations of interest, precipitable cation, and an added displacing salt through a first anion exchange resin material having a precipitable exchangeable polyvalent anion, said displacing salt comprising a displacing polyvalent anion and a counterion to said displacing anion, to displace said precipitable exchangeable polyvalent anion ion from said anion exchange material into said liquid sample under conditions to cause said precipitable cation and exchangeable polyvalent anion to form a precipitate,
   (b) separating from each other the cations of interest in the soluble portion of said liquid sample stream, and
   (c) detecting the separated cations of interest.

16. The method of claim 15 in which said exchangeable anion is selected from the group consisting of sulfate, chromate and phosphate.

17. The method of claim 15 in which said precipitable cation is barium and said exchangeable anion is sulfate.

18. The method of claim 15 in which said displacing anion is tartrate, oxalate, chromate or other divalent or trivalent anions.

19. The method of claim 15 in which said counterion to said displacing anion is silver or barium.

20. The method of claim 15 further comprising, prior to step (c), the step of
   (d) removing said counterion to said displacing anion from said liquid sample stream.

21. The method of claim 20 in which step (d) is performed by passing said liquid sample stream through a second anion exchange resin material having an exchangeable anion capable of precipitation with said counterion to said displacing anion.

* * * * *